(12) United States Patent
Otto et al.

(10) Patent No.: US 12,220,183 B2
(45) Date of Patent: Feb. 11, 2025

(54) SYSTEMS AND METHODS FOR ADAPTIVE PLANNING AND CONTROL OF A SURGICAL TOOL

(71) Applicant: MAKO Surgical Corp., Weston, FL (US)

(72) Inventors: Jason Otto, Sioux Falls, SD (US); Abdullah Abbasi, Lake Worth, FL (US)

(73) Assignee: MAKO Surgical Corp., Weston, FL (US)

( * ) Notice: Subject to any disclaimer, the term of this patent is extended or adjusted under 35 U.S.C. 154(b) by 99 days.

(21) Appl. No.: 17/961,262

(22) Filed: Oct. 6, 2022

(65) Prior Publication Data

US 2023/0024464 A1 Jan. 26, 2023

Related U.S. Application Data

(63) Continuation of application No. 16/427,141, filed on May 30, 2019, now Pat. No. 11,523,870.

(60) Provisional application No. 62/679,185, filed on Jun. 1, 2018.

(51) Int. Cl.
*A61B 34/20* (2016.01)
*A61B 34/00* (2016.01)
*A61B 34/10* (2016.01)
*A61B 34/30* (2016.01)

(52) U.S. Cl.
CPC .............. *A61B 34/20* (2016.02); *A61B 34/10* (2016.02); *A61B 34/25* (2016.02); *A61B 34/30* (2016.02); *A61B 34/76* (2016.02); *A61B 2034/102* (2016.02); *A61B 2034/107* (2016.02); *A61B 2034/2055* (2016.02); *A61B 2034/2065* (2016.02)

(58) Field of Classification Search
CPC ......... A61B 34/20; A61B 34/10; A61B 34/30; A61B 2034/107; A61B 2034/2065
See application file for complete search history.

(56) References Cited

U.S. PATENT DOCUMENTS

| | | | |
|---|---|---|---|
| 8,010,180 B2 * | 8/2011 | Quaid | A61B 34/71 600/426 |
| 9,588,583 B2 | 3/2017 | Lightcap et al. | |
| 10,335,236 B1 | 7/2019 | Murphy et al. | |
| 11,068,882 B1 | 7/2021 | Johnson et al. | |
| 2008/0077158 A1 | 3/2008 | Haider et al. | |

(Continued)

FOREIGN PATENT DOCUMENTS

| | | | |
|---|---|---|---|
| WO | WO-2016205915 A1 * | 12/2016 | ............. A61B 34/10 |
| WO | WO-2017/204832 A1 | 11/2017 | |
| WO | WO-2018/103945 | 6/2018 | |

OTHER PUBLICATIONS

Extended European Search Report for EP Application No. 19275070.1, dated Nov. 13, 2019, 10 pages.

*Primary Examiner* — Jason M Ip
(74) *Attorney, Agent, or Firm* — FOLEY & LARDNER LLP

(57) ABSTRACT

A method includes storing a cloud of points reached by a cutting tool during a first stage of modifying a bone with the cutting tool, generating a surface based on the cloud of points, generating a plan for a second stage of modifying the bone with the cutting tool based on a location or rotation of the surface, and using the plan to assist the cutting tool in executing the second stage of modifying the bone.

18 Claims, 10 Drawing Sheets

(56) References Cited

U.S. PATENT DOCUMENTS

| | | | |
|---|---|---|---|
| 2010/0073150 A1* | 3/2010 | Olson | A61B 34/74 340/407.1 |
| 2011/0190774 A1* | 8/2011 | Nikolchev | A61B 34/10 606/86 R |
| 2011/0208256 A1* | 8/2011 | Zuhars | A61F 2/30942 606/86 R |
| 2012/0123418 A1 | 5/2012 | Giurgi et al. | |
| 2012/0323244 A1 | 12/2012 | Cheal et al. | |
| 2013/0211421 A1 | 8/2013 | Abovitz et al. | |
| 2014/0031664 A1 | 1/2014 | Kang et al. | |
| 2014/0107471 A1 | 4/2014 | Haider et al. | |
| 2014/0180290 A1 | 6/2014 | Otto et al. | |
| 2015/0182288 A1 | 7/2015 | Greenwald et al. | |
| 2016/0022374 A1 | 1/2016 | Haider et al. | |
| 2016/0214255 A1* | 7/2016 | Uhlenbrock | B25J 9/1674 |
| 2017/0258526 A1 | 9/2017 | Lang | |
| 2017/0340389 A1 | 11/2017 | Otto et al. | |
| 2017/0360512 A1 | 12/2017 | Couture et al. | |

* cited by examiner

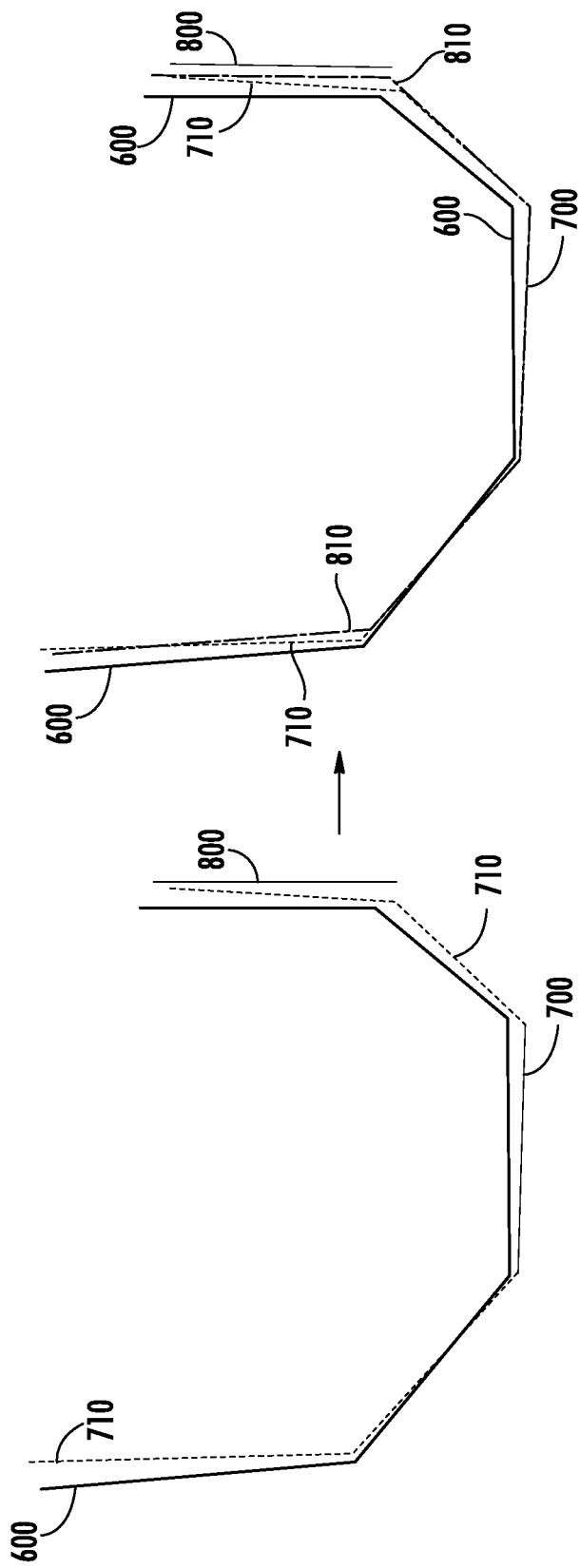

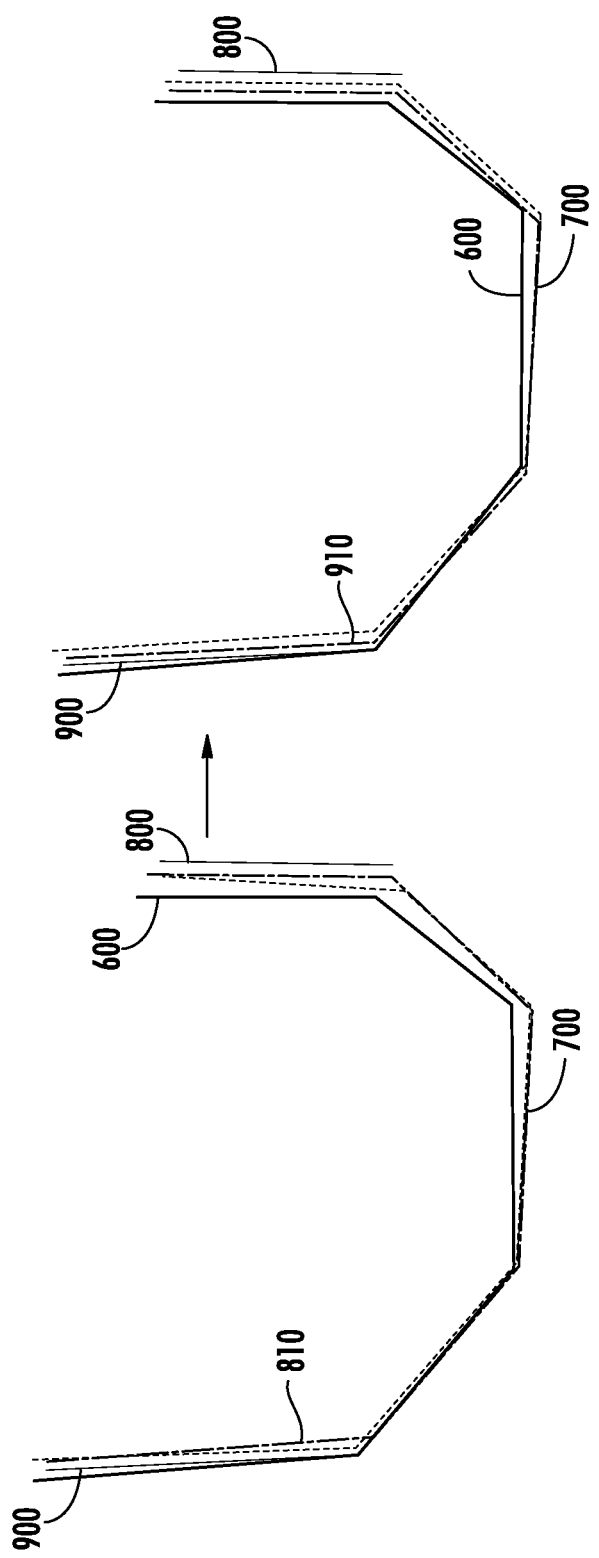

SYSTEMS AND METHODS FOR ADAPTIVE PLANNING AND CONTROL OF A SURGICAL TOOL

CROSS-REFERENCE TO RELATED APPLICATIONS

This application is a continuation of U.S. Ser. No. 16/427,141, filed May 30, 2019, which claims the benefit of and priority to U.S. Provisional Patent Application No. 62/679,185, filed Jun. 1, 2018, the entireties of which are incorporated by reference herein.

BACKGROUND

The present disclosure relates generally to surgical systems for orthopedic surgeries, and more particularly to surgical systems for total knee arthroplasty procedures. Total knee arthroplasty, colloquially referred to as knee replacement, is widely used to treat knee osteoarthritis and other damage to a patient's knee joint by replacing portions of the knee anatomy with prosthetic components. In a total knee arthroplasty procedure, for example, a patient's femur is typically modified to be joined to a prosthesis using a series of planar cuts to prepare the surface of the bone. The relative angle and distance between the cuts is crucial for effectively coupling the prosthesis to the patient's femur and the overall success of the procedure.

One possible tool for use in total knee arthroplasty procedure is a robotically-assisted surgical system. A robotically-assisted surgical system typically includes a robotic device that is used to prepare a patient's anatomy, such as by making bone cuts, a tracking system configured to monitor the location of the robotic device relative to the patient's anatomy, and a computing system configured to monitor and control the robotic device. Robotically-assisted surgical systems, in various forms, autonomously carry out surgical tasks, provide force feedback to a user manipulating a surgical device to complete surgical tasks, augment surgeon dexterity and precision, and/or provide other navigational cues to facilitate safe and accurate surgical operations.

A surgical plan is typically established prior to performing a surgical procedure with a robotically-assisted surgical system. The surgical plan may be patient-specific. Based on the surgical plan, the surgical system guides, controls, or limits movements of the surgical tool during portions of the surgical procedure. Guidance and/or control of the surgical tool serves to protect the patient and to assist the surgeon during implementation of the surgical plan. In a total knee arthroplasty operation, a robotically-assisted surgical system can be used to help carry out a surgical plan that includes making the necessary planar cuts mentioned above, for example by providing force feedback to guide a cutting tool to make the pre-planned planar cuts under surgeon control.

Each actual cut may result in some amount of error in the actual position and orientation of the cut relative to the planned cut. For example, error may be caused by technical limitations of surgical tools including robotic devices, limitations on surgeon dexterity, perception, skill, and/or surgeon mistakes. When multiple cuts, each with its own error, are made according to a pre-established plan, the errors for individual cuts often compound to cause substantial relative errors between cuts, for example increasing an angle between adjacent cuts or decreasing the distance between two cuts. These relative cutting errors may lead to the need for harmful and time-consuming corrective cuts, difficulty in coupling a prosthetic component to the patient's femur, misaligned prosthetic components, and other surgical complications.

BRIEF DESCRIPTION OF THE DRAWINGS

FIGS. 8A-B are cross-sectional views of the surgical plans of FIGS. 5A-7B with a recorded posterior cut plane and the planned cuts of a second updated surgical plan as in the process of FIG. 4, according to an exemplary embodiment.

FIGS. 9A-B are cross-sectional views of the surgical plans of FIGS. 5A-8B with a recorded anterior cut plane and the planned cuts of a third updated surgical plan as in the process of FIG. 4, according to an exemplary embodiment.

DETAILED DESCRIPTION

Figure 1A:
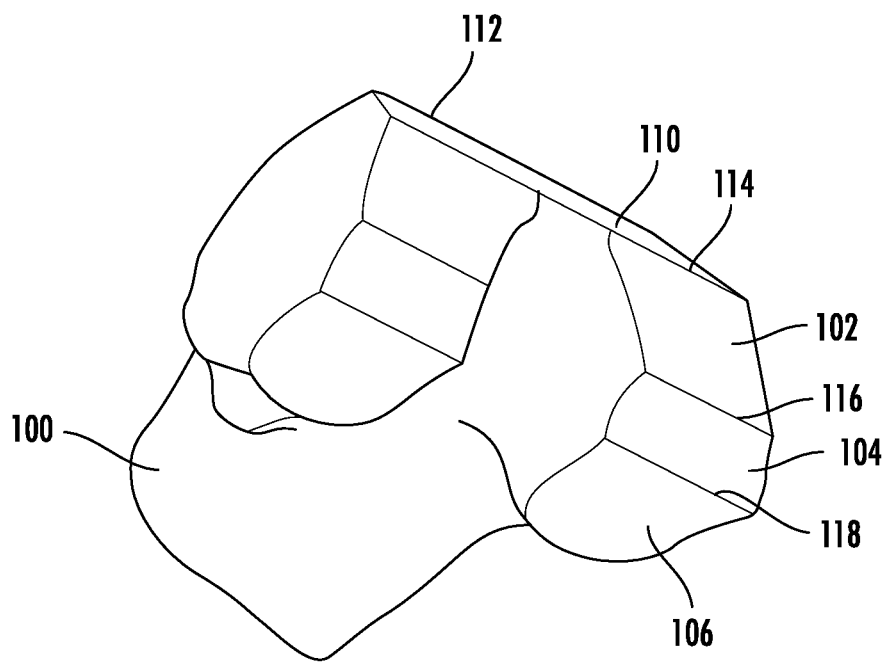
FIG. 1A is a first perspective view of a portion of a femur as prepared in a total knee arthroplasty procedure, according to an exemplary embodiment.
Figure 1B:
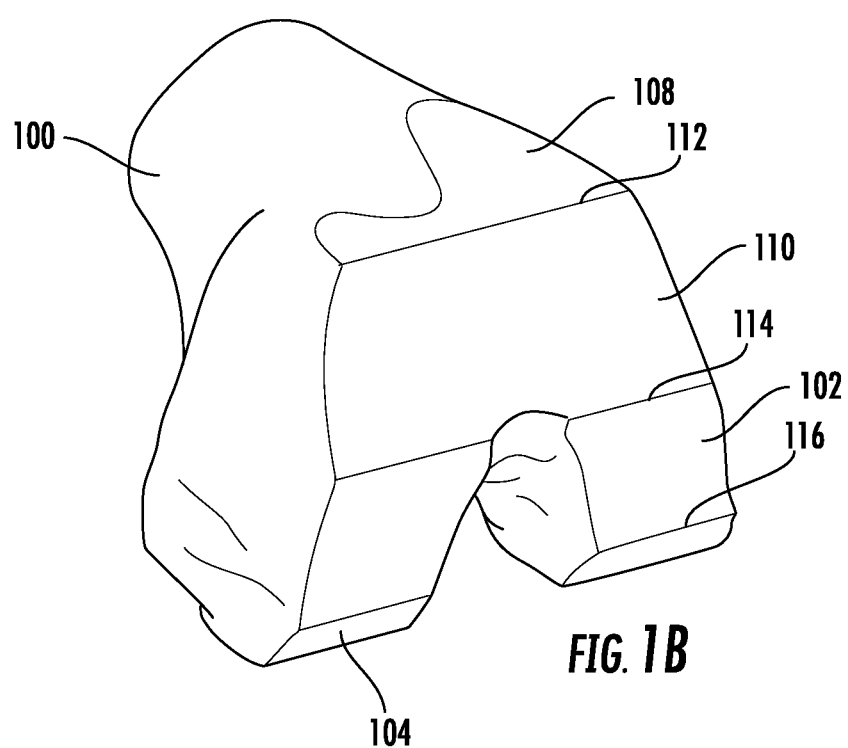
FIG. 1B is a second perspective view of a portion of a femur as prepared in a total knee arthroplasty procedure, according to an exemplary embodiment.

Referring to FIGS. 1A-1B, a portion of a femur 100 prepared to receive a prosthetic component in a total knee arthroplasty procedure is shown. The portion of the femur 100 shown in FIGS. 1A-1B is the distal end of the femur, i.e., the portion that interacts with the tibia in the knee joint. The femur 100 has been modified by five substantially planar cuts to create five substantially planar surfaces, namely distal surface 102, posterior chamfer surface 104, posterior surface 106, anterior surface 108, and anterior chamfer surface 110. The anterior surface 108 shares an edge 112 with anterior chamfer surface 110, which shares an edge 114 with distal surface 102, which shares an edge 116 with posterior chamfer surface 104, which shares an edge 118 with posterior surface 106. The creation of five planar cuts as shown in FIGS. 1A-1B and described elsewhere herein are provided as an example only, and any number of planar cuts may be planned and modified in the same fashion described herein. Furthermore, the same and similar aspects described herein can be similarly applied to preparation of any bone of a joint.

The surfaces 102-110 can be defined by their angles and positions relative to one another and to the femur 100, for example as defined by a reference coordinate system. When oriented and positioned as in FIGS. 1A-B, precise relative orientation and positioning allows surfaces 102-110 to be abutted flush against a femoral component (not shown) of a knee prosthesis with a matching geometrical structure (e.g., with a set of surfaces oriented and shaped like surfaces 102-110). In such a case, the femoral component is then also properly aligned with the femur 100, other prosthetic components, and other anatomical features to provide positive surgical outcomes for a patient (e.g., short recovery times, full range of motion, pain-free mobility, long-term reliability).

However, because of technical limitations and bounds on surgeon perception and dexterity and/or on available surgical tools, some amount of error in the cuts that create the surfaces 102-110 is common. Error in the relative position or angle of the surfaces 102-110 may prevent the femur from properly engaging a prosthetic device. Because each surface 102-110 is connected to another surface 102-110 along at least one edge 112-118, an error in the orientation or position of one surface is likely to cause a distortion in one or more neighboring surfaces. For example, if the distal surface 102 is shifted to be oriented at a greater angle relative to the anterior chamfer surface 110, a distance and angle between the distal surface 102 and the posterior chamfer surface 104 may also be distorted. The overall shape created by the surfaces 102-110, then, is also distorted. In such a case, the femoral component of a prosthetic device may not align properly with surfaces 102-110, potentially causing negative surgical outcomes, the need for follow up procedures, and limited mobility and/or chronic pain for the patient. Thus, a need exists for surgical systems and methods for minimizing the relative cutting error between the five femoral cuts. As described herein, intraoperative updates to a surgical plan for use with a robotically-assisted surgical system can help to minimize relative cutting errors of, for example, femoral cuts of a total knee arthroplasty procedure.

Figure 2:
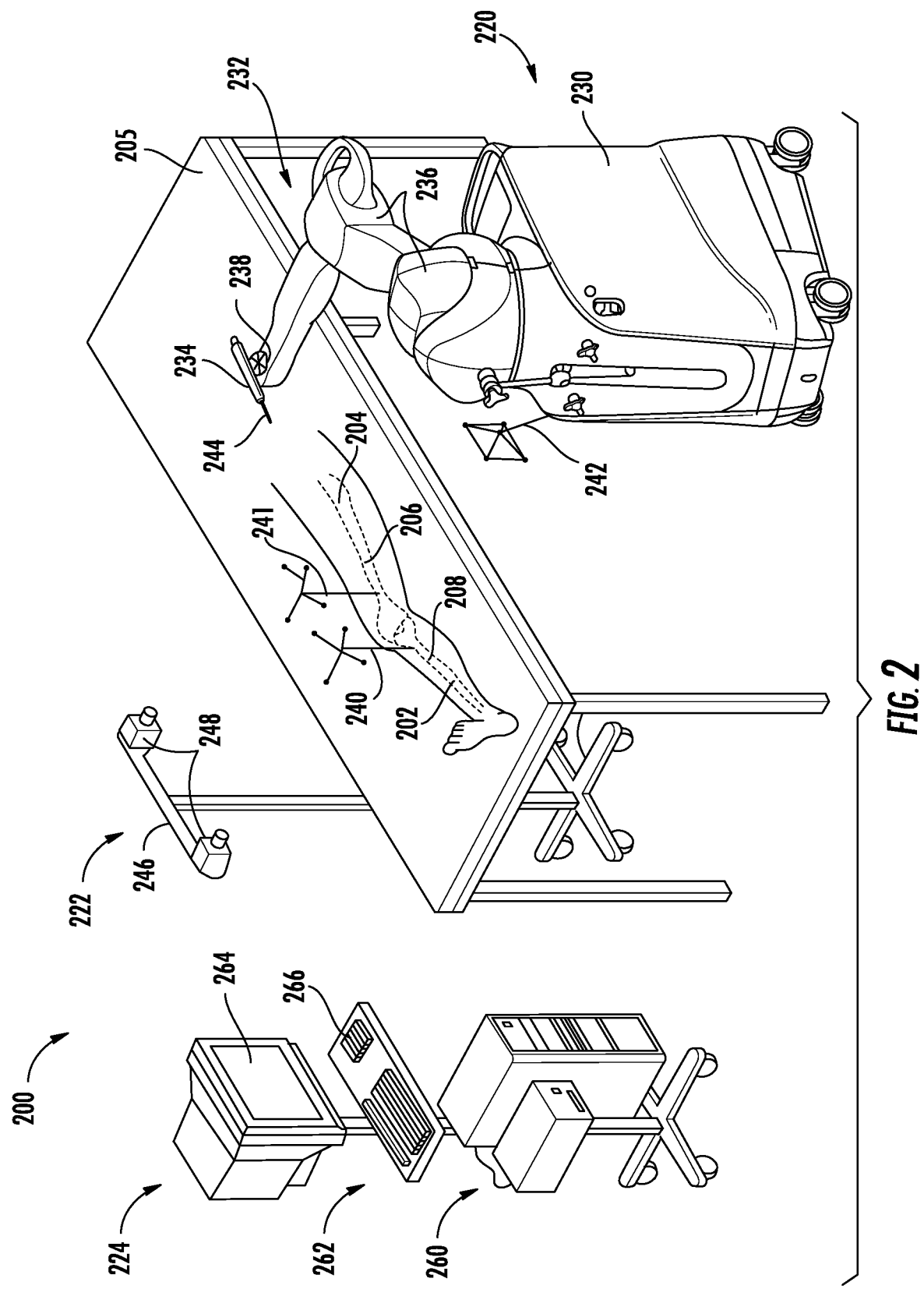
FIG. 2 is an illustration of a surgical system, according to an exemplary embodiment.

Referring now to FIG. 2, a surgical system 200 for orthopedic surgery is shown, according to an exemplary embodiment. In general, the surgical system 200 is configured to facilitate the planning, cutting, and error minimization of cuts required to form surfaces 102-110 of FIG. 1. As shown in FIG. 2, the surgical system 200 is set up to treat a leg 202 of a patient 204 sitting or lying on table 205. Leg 202 includes femur 206 and tibia 208, between which a prosthetic knee implant is to be implanted in a total knee arthroscopy procedure. To facilitate the procedure, surgical system 200 includes robotic device 220, tracking system 222, and computing system 224.

The robotic device 220 is configured to modify a patient's anatomy (e.g., femur 206 of patient 204) under the control of the computing system 224. One embodiment of the robotic device 220 is a haptic device. "Haptic" refers to a sense of touch, and the field of haptics relates to, among other things, human interactive devices that provide feedback to an operator. Feedback may include tactile sensations such as, for example, vibration. Feedback may also include providing force to a user, such as a positive force or a resistance to movement. One use of haptics is to provide a user of the device with guidance or limits for manipulation of that device. For example, a haptic device may be coupled to a surgical tool, which can be manipulated by a surgeon to perform a surgical procedure. The surgeon's manipulation of the surgical tool can be guided or limited through the use of haptics to provide feedback to the surgeon during manipulation of the surgical tool.

Another embodiment of the robotic device 220 is an autonomous or semi-autonomous robot. "Autonomous" refers to a robotic device's ability to act independently or semi-independently of human control by gathering information about its situation, determining a course of action, and automatically carrying out that course of action. For example, in such an embodiment, the robotic device 220, in communication with the tracking system 222 and the computing system 222, may autonomously complete the series of femoral cuts mentioned above without direct human intervention.

The robotic device 220 includes a base 230, a robotic arm 232, and a surgical tool 234, and is communicably coupled to the computing system 224 and the tracking system 222. The base 230 provides a moveable foundation for the robotic arm 232, allowing the robotic arm 232 and the surgical tool 234 to be repositioned as needed relative to the patient 204 and the table 205. The base 230 may also contain power systems, computing elements, motors, and other electronic or mechanical system necessary for the functions of the robotic arm 232 and the surgical tool 234 described below.

The robotic arm 232 is configured to support the surgical tool 234 and provide a force as instructed by the computing system 224. In some embodiments, the robotic arm 232 allows a user to manipulate the surgical tool and provides force feedback to the user. In such an embodiment, the robotic arm 232 includes joints 236 and mount 238 that include motors, actuators, or other mechanisms configured to allow a user to freely translate and rotate the robotic arm 232 and surgical tool 234 through allowable poses while providing force feedback to constrain or prevent some movements of the robotic arm 232 and surgical tool 234 as instructed by computing system 224. As described in detail below, the robotic arm 232 thereby allows a surgeon to have full control over the surgical tool 234 within a control object while providing force feedback along a boundary of that object (e.g., a vibration, a force preventing or resisting penetration of the boundary). In some embodiments, the robotic arm is configured to move the surgical tool to a new pose automatically without direct user manipulation, as instructed by computing system 224, in order to position the robotic arm as needed and/or complete certain surgical tasks, including, for example, cuts in a femur 206.

The surgical tool 234 is configured to cut, grind, drill, partially resect, reshape, and/or otherwise modify a bone. More particularly, for preparation of a distal femur having five planar cuts, surgical tool 234 is configured to make a distal cut, a posterior chamfer cut, a posterior cut, an anterior cut, and an anterior chamfer cut in femur 206 to create the distal surface 102, posterior chamfer surface 104, posterior surface 106, anterior surface 108, and anterior chamfer surface 110 as shown in FIG. 1 (i.e., to reshape femur 206 like femur 100). The surgical tool 234 may be any suitable tool, and may be one of multiple tools interchangeably connectable to robotic device 220. For example, as shown in FIG. 2 the surgical tool 234 is a spherical burr. The surgical tool may also be a sagittal saw, for example with a blade aligned parallel with a tool axis or perpendicular to the tool axis.

Tracking system 222 is configured track the patient's anatomy (e.g., femur 206 and tibia 208) and the robotic device 220 (i.e., surgical tool 234 and/or robotic arm 232) to enable control of the surgical tool 234 coupled to the robotic arm 232, to determine a position and orientation of cuts made by the surgical tool 234, and allow a user to visualize the femur 206, the tibia 208, the surgical tool 234, and/or the robotic arm 232 on a display of the computing system 224.

More particularly, the tracking system 222 determines a position and orientation (i.e., pose) of objects (e.g., surgical tool 234, femur 206) with respect to a coordinate frame of reference and tracks (i.e., continuously determines) the pose of the objects during a surgical procedure. According to various embodiments, the tracking system 222 may be any type of navigation system, including a non-mechanical tracking system (e.g., an optical tracking system), a mechanical tracking system (e.g., tracking based on measuring the relative angles of joints 236 of the robotic arm 232), or any combination of non-mechanical and mechanical tracking systems.

In the embodiment shown in FIG. 2, the tracking system 222 includes an optical tracking system. Accordingly, tracking system 222 includes a first fiducial tree 240 coupled to the tibia 208, a second fiducial tree 241 coupled to the femur 206, a third fiducial tree 242 coupled to the base 230, one or more fiducials 244 coupled to surgical tool 234, and a detection device 246 configured to detect the three-dimensional position of fiducials (i.e., markers on fiducial trees 240-242). As shown in FIG. 2, detection device 246 includes a pair of cameras 248 in a stereoscopic arrangement. The fiducial trees 240-242 include fiducials, which are markers configured to show up clearly to the cameras 248 and/or be easily detectable by an image processing system using data from the cameras 248, for example by being highly reflective of infrared radiation (e.g., emitted by an element of tracking system 222). The stereoscopic arrangement of the cameras 248 on detection device 246 allows the position of each fiducial to be determined in 3D-space through a triangulation approach. Each fiducial has a geometric relationship to a corresponding object, such that tracking of the fiducials allows for the tracking of the object (e.g., tracking the second fiducial tree 241 allows the tracking system 222 to track the femur 206), and the tracking system 222 may be configured to carry out a registration process to determine or verify this geometric relationship. Unique arrangements of the fiducials in the fiducial trees 240-242 (i.e., the fiducials in the first fiducial tree 240 are arranged in a different geometry than fiducials in the second fiducial tree 241) allows for distinguishing the fiducial trees, and therefore the objects being tracked, from one another.

Using the tracking system 222 of FIG. 2 or some other approach to surgical navigation and tracking, the surgical system 200 can determine the position of the surgical tool 234 relative to a patient's anatomical feature, for example femur 206, as the surgical tool 234 is used to make a cut in or otherwise modify the anatomical feature.

The computing system 224 is configured to create a surgical plan, control the robotic device 220 in accordance with the surgical plan to make one or more surgical cuts, receive data relating to the location of the surgical tool 234, determine the location and orientation of cuts made by the surgical tool 234, alter the surgical plan based on the determinations to minimize the relative error between cuts, and control the robotic device in accordance with the updated surgical plan. Accordingly, the computing system 224 is communicably coupled to the tracking system 222 and the robotic device 220 to facilitate electronic communication between the robotic device 220, the tracking system 222, and the computing system 224. Further, the computing system 224 may be connected to a network to receive information related to a patient's medical history or other patient profile information, medical imaging, surgical plans, surgical procedures, and to perform various functions related to performance of surgical procedures, for example by accessing an electronic health records system. Computing system 224 includes processing circuit 260 and input/output device 262.

The input/output device 262 is configured to receive user input and display output as needed for the functions and processes described herein. As shown in FIG. 2, input/output device 262 includes a display 264 and a keyboard 266. The display 264 is configured to display graphical user interfaces generated by the processing circuit 260 that include, for example, information about surgical plans, medical imaging, settings and other options for surgical system 200, status information relating to the tracking system 222 and the robotic device 220, and tracking visualizations based on data supplied by tracking system 222. The keyboard 266 is configured to receive user input to those graphical user interfaces to control one or more functions of the surgical system 200.

The processing circuit 260 includes a processor and memory device. The processor can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit 260 and includes computer code for executing (e.g., by the processing circuit 260 and/or processor) one or more processes described herein.

More particularly, processing circuit 260 is configured to facilitate the creation of a preoperative surgical plan prior to the surgical procedure. According to some embodiments, the preoperative surgical plan is developed utilizing a three-dimensional representation of a patient's anatomy, also referred to herein as a "virtual bone model." A "virtual bone model" may include virtual representations of cartilage or other tissue in addition to bone. To obtain the virtual bone model, the processing circuit 260 receives imaging data of the patient's anatomy on which the surgical procedure is to be performed (e.g., femur 206). The imaging data may be created using any suitable medical imaging technique to image the relevant anatomical feature, including computed tomography (CT), magnetic resonance imaging (MRI), and/or ultrasound. The imaging data is then segmented (i.e., the regions in the imaging corresponding to different anatomical features are distinguished) to obtain the virtual bone model. For example, MRI-based scan data of a knee is segmented to distinguish the femur from surrounding ligaments, cartilage, and other tissue to obtain a three-dimensional model of the imaged femur.

Alternatively, the virtual bone model may be obtained by selecting a three-dimensional model from a database or library of bone models. In one embodiment, the user may use input/output device 262 to select an appropriate model. In another embodiment, the processing circuit 260 may execute stored instructions to select an appropriate model based on images or other information provided about the patient. The selected bone model(s) from the database can then be deformed based on specific patient characteristics, creating a virtual bone model for use in surgical planning and implementation as described herein.

A preoperative surgical plan can then be created based on the virtual bone model. The surgical plan may be automatically generated by the processing circuit 260, input by a user via input/output device 262, or some combination of the two (e.g., the processing circuit 260 limits some features of user-created plans, generates a plan that a user can modify, etc.).

The preoperative surgical plan includes the desired cuts, holes, or other modifications to a patient's anatomy to be made using the surgical system 200. More particularly, for a total knee arthroscopy procedure as described herein, the preoperative plan includes the cuts necessary to form distal surface 102, posterior chamfer surface 104, posterior surface 106, anterior surface 108, and anterior chamfer surface 110 in ideal relative orientations and positions. The pre-planned positions and orientations of the surfaces 102-110 are based on the geometry of the prosthetic to be joined to the surfaces 102-110 during the surgical procedure and information about the patient. Accordingly, the processing circuit 260 may receive, access, and/or store a model of the prosthetic to facilitate the generation of surgical plans.

The processing circuit 260 is further configured to generate a control object for the robotic device 220 in accordance with the surgical plan. The control object may take various forms according to the various types of possible robotic devices (e.g., haptic, autonomous, etc). For example, in some embodiments, the control object defines instructions for the robotic device to control the robotic device to move within the control object (i.e., to autonomously make one or more cuts of the surgical plan guided by feedback from the tracking system 222). In some embodiments, the control object includes a visualization of the surgical plan and the robotic device on the display 264 to facilitate surgical navigation and help guide a surgeon to follow the surgical plan (e.g., without active control or force feedback of the robotic device). In embodiments where the robotic device 220 is a haptic device, the control object may be a haptic object as described in the following paragraphs.

In an embodiment where the robotic device 220 is a haptic device, the processing circuit 260 is further configured to generate one or more haptic objects based on the preoperative surgical plan to assist the surgeon during implementation of the surgical plan by enabling constraint of the surgical tool 234 during the surgical procedure. A haptic object may be formed in one, two, or three dimensions. For example, a haptic object can be a line, a plane, or a three-dimensional volume. A haptic object may be curved with curved surfaces and/or have flat surfaces, and can be any shape, for example a funnel shape. Haptic objects can be created to represent a variety of desired outcomes for movement of the surgical tool 234 during the surgical procedure. One or more of the boundaries of a three-dimensional haptic object may represent one or more modifications, such as cuts, to be created on the surface of a bone. A planar haptic object may represent a modification, such as a cut, to be created on the surface of a bone (e.g., corresponding to the creation of surfaces 102-110).

In an embodiment where the robotic device 220 is a haptic device, the processing circuit 260 is further configured to generate a virtual tool representation of the surgical tool 234. The virtual tool includes one or more haptic interaction points (HIPs), which represent and are associated with locations on the physical surgical tool 234. In an embodiment in which the surgical tool 234 is a spherical burr (e.g., as shown in FIG. 2), an HIP may represent the center of the spherical burr. If the surgical tool 234 is an irregular shape, for example as for a sagittal saw, the virtual representation of the sagittal saw may include numerous HIPs. Using multiple HIPs to generate haptic forces (e.g. positive force feedback or resistance to movement) on a surgical tool is described in U.S. application Ser. No. 13/339,369, titled "System and Method for Providing Substantially Stable Haptics," filed Dec. 28, 2011, and hereby incorporated by reference herein in its entirety. In one embodiment of the present invention, a virtual tool representing a sagittal saw includes eleven HIPs. As used herein, references to an "HIP" are deemed to also include references to "one or more HIPs." As described below, relationships between HIPs and haptic objects enable the surgical system 200 to constrain the surgical tool 234.

Prior to performance of the surgical procedure, the patient's anatomy (e.g., femur 206) is registered to the virtual bone model of the patient's anatomy by any known registration technique. One possible registration technique is point-based registration, as described in U.S. Pat. No. 8,010,180, titled "Haptic Guidance System and Method," granted Aug. 30, 2011, and hereby incorporated by reference herein in its entirety. Alternatively, registration may be accomplished by 2D/3D registration utilizing a hand-held radiographic imaging device, as described in U.S. application Ser. No. 13/562,163, titled "Radiographic Imaging Device," filed Jul. 30, 2012, and hereby incorporated by reference herein in its entirety. Registration also includes registration of the surgical tool 234 to a virtual tool representation of the surgical tool 234, so that the surgical system 200 can determine and monitor the pose of the surgical tool 234 relative to the patient (i.e., to femur 206). Registration of allows for accurate navigation, control, and/or force feedback during the surgical procedure.

The processing circuit 260 is configured to monitor the virtual positions of the virtual tool representation, the virtual bone model, and the control object (e.g., virtual haptic objects) corresponding to the real-world positions of the patient's bone (e.g., femur 206), the surgical tool 234, and one or more lines, planes, or three-dimensional spaces defined by forces created by robotic device 220. For example, if the patient's anatomy moves during the surgical procedure as tracked by the tracking system 222, the processing circuit 260 correspondingly moves the virtual bone model. The virtual bone model therefore corresponds to, or is associated with, the patient's actual (i.e. physical) anatomy and the position and orientation of that anatomy in real/physical space. Similarly, any haptic objects, control objects, or other planned automated robotic device motions created during surgical planning that are linked to cuts, modifications, etc. to be made to that anatomy also move in correspondence with the patient's anatomy. In some embodiments, the surgical system 200 includes a clamp or brace to substantially immobilize the femur 206 to minimize the need to track and process motion of the femur 206.

For embodiments where the robotic device 220 is a haptic device, the surgical system 200 is configured to constrain the surgical tool 234 based on relationships between HIPs and haptic objects. That is, when the processing circuit 260 uses data supplied by tracking system 222 to detect that a user is manipulating the surgical tool 234 to bring a HIP in virtual contact with a haptic object, the processing circuit 260 generates a control signal to the robotic arm 232 to provide haptic feedback (e.g., a force, a vibration) to the user to communicate a constraint on the movement of the surgical tool 234. In general, the term "constrain," as used herein, is used to describe a tendency to restrict movement. However, the form of constraint imposed on surgical tool 234 depends on the form of the relevant haptic object. A haptic object may be formed in any desirable shape or configuration. As noted above, three exemplary embodiments include a line, plane, or three-dimensional volume. In one embodiment, the surgical tool 234 is constrained because a HIP of surgical tool 234 is restricted to movement along a linear haptic object. In another embodiment, the haptic object is a three-dimensional volume and the surgical tool 234 may be constrained by substantially preventing movement of the HIP outside of the volume enclosed by the walls of the three-dimensional haptic object. In another embodiment, the surgical tool 234 is constrained because a planar haptic object substantially prevents movement of the HIP outside of the plane and outside of the boundaries of the planar haptic object. For example, the processing circuit 260 can establish a planar haptic object corresponding to a planned planar distal cut needed to create a distal surface 102 on femur 206 in order to confine the surgical tool 234 substantially to the plane needed to carry out the planned distal cut.

For embodiments where the robotic device 220 is an autonomous device, the surgical system 200 is configured to autonomously move and operate the surgical tool 234 in accordance with the control object. For example, the control object may define areas relative to the femur 206 for which a cut should be made. In such a case, one or more motors, actuators, and/or other mechanisms of the robotic arm 232 and the surgical tool 234 are controllable to cause the surgical tool 234 to move and operate as necessary within the control object to make a planned cut, for example using tracking data from the tracking system 222 to allow for closed-loop control.

The processing circuit 260 is further configured to record and store the instantaneous position of a tool center point (TCP) of the surgical tool 234 (e.g., the location of the virtual tool representation relative to the virtual bone model) based on data provided by the tracking system 222 as the surgical tool 234 carries out the preoperative surgical plan. As discussed in detail below with reference to FIGS. 3-10, the processing circuit 260 uses recorded TCP positions of the surgical tool 234 to determine deviations from the surgical plan and updates the preoperative surgical plan to intraoperatively update the surgical plan to minimize the relative error between multiple cuts. In some embodiments, the tracking of the TCP may be of a higher accuracy or resolution than the haptic objects, a surgeon's perception or dexterity, and/or the tolerances of automated robotic movements such that errors in cuts (i.e., deviations from planned cuts) that were made using the surgical system 200 can be determined and quantified. As described in further detail below with reference to FIGS. 3-10, the processing circuit 260 is configured to use the recorded tool center point positions to determine the location and orientation of cuts made by the surgical tool 234, compare these locations and orientations to the surgical plan, and update the surgical plan for subsequent cuts to minimize the relative error between cuts.

Figure 3:
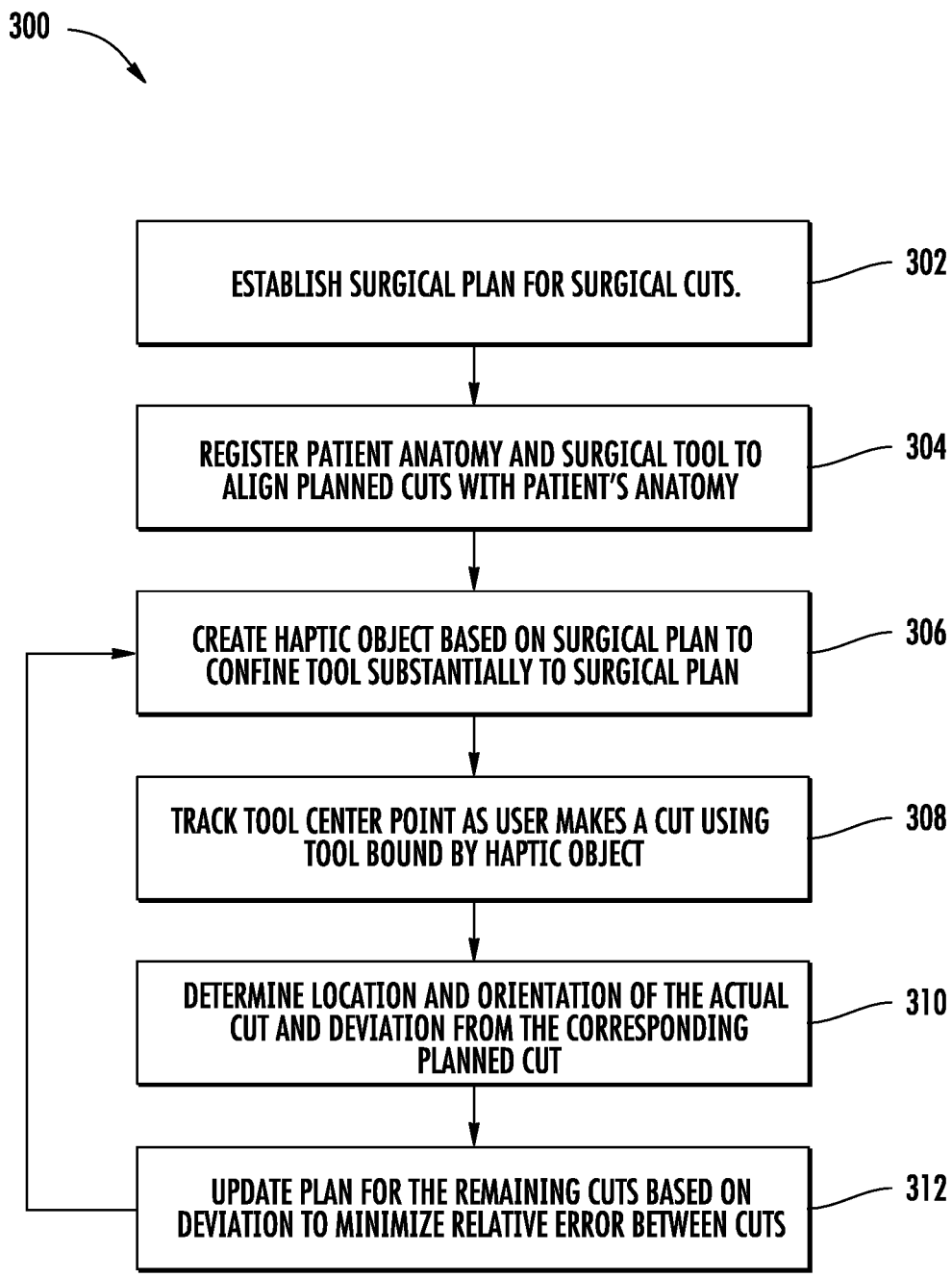
FIG. 3 is a flowchart of a process for minimizing relative cutting errors in a total knee arthroplasty procedure, according to an exemplary embodiment.

Referring now FIG. 3, a flowchart showing a process 300 for minimizing relative error in cuts made with a robotically-assisted surgical system in a surgical procedure is shown, according to an exemplary embodiment. The process 300 can be carried out by the surgical system 200 shown in FIG. 2, for example as part of a total knee arthroplasty procedure. Accordingly, for the sake of clarity, reference is made to elements of the surgical system 200 in the following description.

At step 302, a surgical plan is established that includes multiple surgical cuts to be carried out by a surgical tool. For example, processing circuit 260 may automatically generate a surgical plan based on imaging data of a patient and/or other information related to the patient and/or the procedure. In some embodiments, a surgeon or other user creates or modifies the surgical plan using input/output device 262 of computing system 224.

At step 304, a registration process is carried out to register the patient anatomy and surgical tool to align the planned cuts with the patient's anatomy. For example, the registration process may be carried out by the tracking system 222 in communication with the processing circuit 260 to register a virtual bone model to a physical bone of the patient (e.g., femur 206) and a HIP to the surgical tool 234. As mentioned above, the registration process may be any suitable registration process. The registration process includes determining the coordinates of the physical bone, the preplanned cuts, and the surgical tool within a Euclidean coordinate system used by the processing circuit 260.

At step 306, a control object is created by the processing circuit 260 to facilitate the surgical tool 234 in making the planned cuts consistent with the surgical plan. For example, the planned cuts may be defined by planes aligned with desired post-cut surfaces of a bone (e.g., surfaces 102-110 of FIG. 1), such that a control object (e.g., a haptic object) includes a planar control object for each of the planned cuts that substantially confines the surgical tool to move in the plane necessary to make the cut (e.g., in planes coplanar with surfaces 102-110 of FIG. 1). In some embodiments, a haptic object is configured to confine the surgical tool to complete the planned cuts in a particular order, for example by confining the surgical tool to a first planar haptic object until the first cut is made, and then confining the surgical tool to a second planar haptic object until the second cut is made, and so on.

At step 308, the tool center point (TCP) of the surgical tool is tracked as the first cut is made (e.g., by a surgeon as confined by a haptic object or autonomously by the robotic device 220). The TCP may be tracked by the tracking system 222, for example based on a fiducial 244 mounted on the surgical tool 234. The processing circuit 260 records instantaneous positions of the TCP within a pre-defined Euclidean space. In some embodiments, the TCP is the central point of the distal end of an end effector of the surgical tool 234, or has a known geometric relationship with an effective end of the surgical tool 234 (i.e., the point on the tool that cuts, saws, files, grinds, etc. a bone), so that the TCP corresponds to a position of a modification to the patient anatomy made by the end effector. In some embodiments, the tracking system 222 and the computing system 224 track the tool center point with a higher accuracy or resolution than a surgeon can make a cut, than the robotic device 230 can move the surgical tool 234, and/or than a haptic boundary can confine the surgical tool, such that tracking the tool center point may be used to determine a deviation from a planned cut.

At step 310, the location and orientation of the cut and the deviation from the corresponding planned cut are determined. The location and orientation of the cut may be determined by the processing circuit 260 by identifying tracked TCP positions that correspond to the cut and fitting a plane to the identified TCP positions. For example, TCP positions may be continuously recorded as the surgical tool is moved into position to make the cut, as a partial cuts are made, or as a multi-stage cut is made, such that the TCP positions corresponding to the deepest or most impactful motions of the surgical tool (i.e., the movements that remove the most bone or a deepest layer of bone) are identified by the processing circuit 260 as the TCP positions relevant to determining the location and orientation of the cut. In some cases, the relevant TCP positions are those which are positioned along a surface of a 3-D cloud of recorded TCP positions. The processing circuit 260 then fits a plane ("recorded cut plane") to the relevant TCP positions (e.g., defining a surface of the 3-D cloud of recorded TCP positions). The processing circuit 260 may use any three-dimensional data-fitting technique to fit the recorded cut plane to the recorded TCP positions.

The processing circuit 260 then compares the recorded cut plane to the planned cut to determine the deviation between the recorded cut plane (i.e., the real-world, actual cut) and the planned cut. The deviation may include a translational deviation and/or a rotational deviation. The translational deviation is determined by calculating the shortest distance between the centroid of the planned cut to the recorded cut plane. The rotational deviation is determined by calculating the degree to which the recorded cut plane is rotated about one or more axes (e.g., of the Euclidean coordinate system, of the planned cut) relative to planned cut.

At step 312, based on the calculated deviations, the processing circuit 260 updates the surgical plan for the remaining planned cuts to minimize the relative error between cuts. An embodiment of this process is described in detail with respect to FIGS. 4-10. According to some embodiments, minimizing the relative error between cuts includes preserving an originally-planned overall shape formed by the planned cuts to the greatest possible extent. Error minimization may also take into consideration the relative error in the position and orientation of the cuts relative to the patient's bone, other anatomical features, other surgical steps, or prosthetic components.

After the surgical plan is updated at step 312, the process returns to step 306, where an updated control object is created (or modified from a control object formed previously) based on the updated surgical plan, as described above. A second cut is made while the TCP is tracked at step 308, as described above for the first cut. At step 310, the location and orientation of the second actual cut is determined, and the deviation of the second actual cut from the second planned cut (based on the updated surgical plan and/or the original surgical plan) is determined. The surgical plan is against updated based on the deviation at step 312, and the process 300 may return again to step 306.

The process 300 thereby repeatedly loops through steps 306-312 as each planned cut is made. In some embodiments, the surgical plan is updated for every cut made as part of the surgical plan, while in other embodiments the surgical plan is only updated after a portion of the cuts are made. For example, the surgical plan may be updated after alternating cuts or after every third cut. As another example, the surgical plan may be updated only if the deviations determined in step 310 exceed a certain error threshold and/or fall below a certain threshold.

Figure 4:
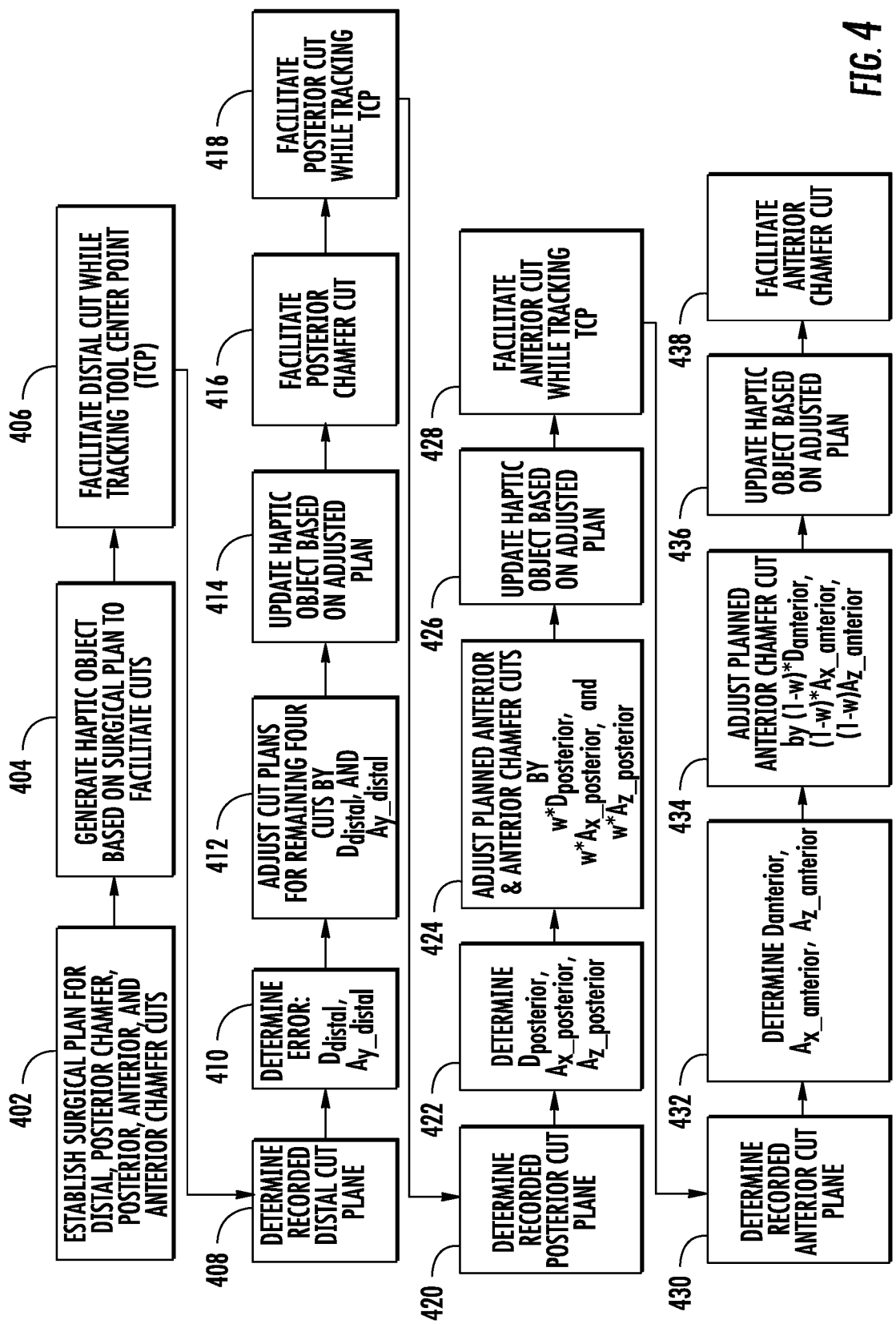
FIG. 4 is a flowchart of another process for minimizing cutting error in a total knee arthroplasty procedure, according to an exemplary embodiment.

Referring now to FIGS. 4-10, a process 400 for relative error minimization in the femoral distal, posterior chamfer, posterior, anterior, and anterior chamfer cuts in a total knee arthroplasty procedure is shown, according to an exemplary embodiment. FIG. 4 shows a flowchart depicting process 400, and FIGS. 5-10 are illustrations useful for explaining the process 400 shown in FIG. 4. Process 400 is an embodiment of process 300 of FIG. 3. As such, process 400 can also be carried out by surgical system 200 of FIG. 2, and, for the sake of clarity, reference is made to components of surgical system 200 in the following description of process 400.

At step 402, a surgical plan is established for the five femoral cuts of a total knee arthroplasty procedure, namely the distal, posterior chamfer, posterior, anterior, and anterior chamfer cuts. According to various embodiments, the surgical plan is automatically generated by processing circuit 260 based on medical imaging data and other patient or procedure related information, input to computing system 224 by a surgeon or other user, imported from an external computing system by the computing system 224 via a network, or some combination of those or other planning procedures.

The surgical plan includes a planned cut for each of the five cuts, in general aimed at modifying a femur (e.g., femur 206) to create surfaces corresponding to distal surface 102, posterior chamfer surface 104, posterior surface 106, anterior surface 108, and anterior chamfer surface 110 of femur 100 shown in FIG. 1. Although various motions of the surgical tool 234 may be required to carry out the planned cuts described herein, the planned cuts and subsequent planned cuts described below are represented by the desired planar surfaces of the femur to be created by the corresponding cuts. Accordingly, each planned cut includes a centroid that defines a central point of the planned cut in a three-dimensional reference Euclidean coordinate system (i.e., to fix a location of the planned cut) and an angular rotation of the planned cut relative to a reference plane around the axes of a Euclidean coordinate system (i.e., an angle relative to the x-axis, y-axis, and/or z-axis to fix an orientation of the planned cut relative to the other planned cuts), as illustrated in FIGS. 5A-5C.

Figure 5A:
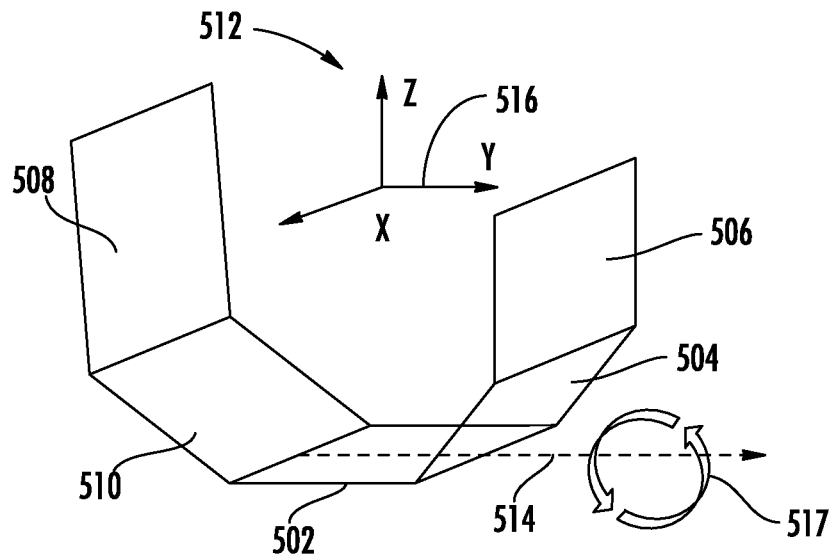
FIGS. 5A-C are visualizations of planned surgical cuts for use in the process of FIG. 4, according to an exemplary embodiment.
Figure 5B:
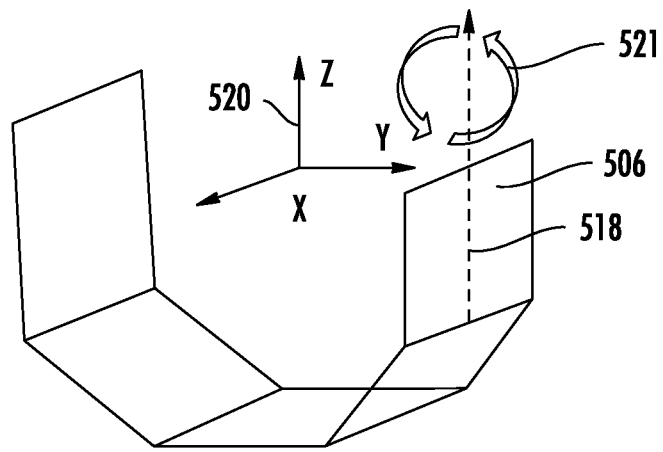
Figure 5C:
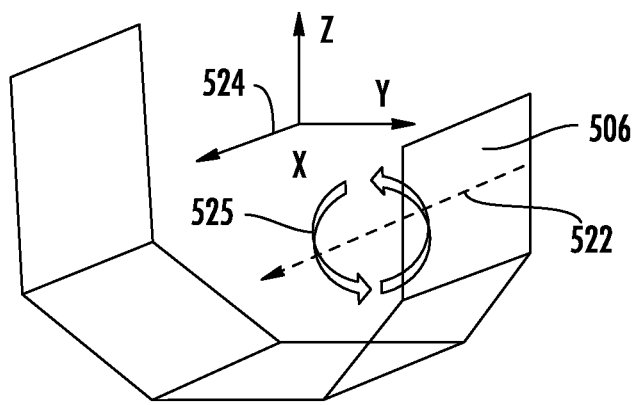

FIGS. 5A-5C show planned cuts 500, namely distal cut 502, posterior chamfer cut 504, posterior cut 506, anterior cut 508, and anterior chamfer cut 510, aligned on a Euclidean coordinate system defined by axes 512. As shown, each cut 502-510 has a position that can be defined by a centroid of the cut, and a relative orientation that can be defined based on rotation about one or more axes 512. For example, in FIG. 5A, a projection 514 of the y-axis 516 on the distal cut 502 shows that the distal cut 502 can be rotated around the y-axis (illustrated by rotation indicator 517). FIG. 5B shows a projection 518 of the z-axis 520 on the posterior cut 506 that shows that the posterior cut 506 can be rotated around the z-axis (illustrated by rotation indicator 521), while FIG. 5C shows a projection 522 of the x-axis 524 on the posterior cut 506 that shows that the posterior cut 506 can be rotated around the x-axis (illustrated by rotation indicator 525). In some embodiments, the planned distal cut 502 is taken as reference planar cut with an origin at its centroid, and the other planned cuts are defined based on a three-dimensional location of a centroid relative to the centroid of the distal cut 502 and the rotations about the axes 516, 520, 524 of the reference coordinate system needed to rotate the distal cut 502 to match the orientation of the other planned cut. As discussed in detail below, errors in the cuts can also be characterized based on rotational errors about the axes 516, 520, 524 and deviations from the locations of the centroids of the planned cuts 502-510.

Figure 6:
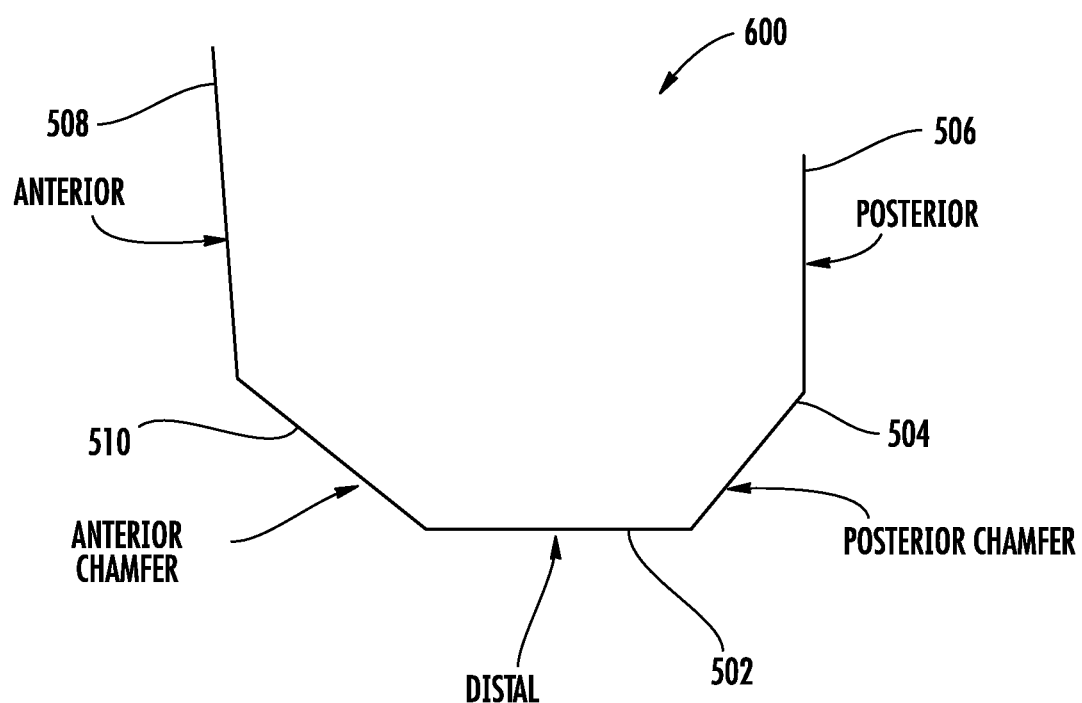
FIG. 6 is a cross-sectional view of the planned surgical cuts of FIGS. 5A-C as in the process of FIG. 4, according to an exemplary embodiment.

The planned cuts 502-510 of the surgical plan established at step 402 of process 400 are shown in FIG. 6 in a cross-sectional view, and referred to collectively in the following as the "original surgical plan" 600. Although each cut 502-510, as described above, is a planar object in three-dimensional space, two-dimensional cross-sectional views are shown in FIGS. 6-10 for clarity and to ease explanation of process 400.

At step 404, the processing circuit 260 generates a control object based on the original surgical plan to facilitate the planned cuts. According to some embodiments, the control object is a haptic object that includes a planar haptic object for each of the planned cuts 502-510, such that the haptic object is configured to confine the surgical tool 234 substantially to the plane needed to make the corresponding cut. In some embodiments, a haptic object generated at step 404 confines the surgical tool 234 substantially to the plane corresponding to the distal cut 502, such that the surgeon must make the distal cut before other cuts. The control object may have any form that controls or otherwise facilitates the surgical tool 234 of robotic device 220 to making the planned cuts.

At step 406, the surgical system 200 facilitates the distal cut while tracking the tool center point (TCP) of the surgical tool 234. According to some embodiments, step 406 includes a registration step to register the planned cuts 502-510 and the corresponding control object to the patient's real-world anatomy (i.e., femur 206), as well as register the surgical tool 234 to the same coordinate system, for example as described in reference to step 304 of FIG. 3. The TCP can then by tracked by tracking system 222, with TCP positions determinable relative to the planned cuts 502-510 and the patient's femur 206. In embodiments involving a haptic object, one or more HIPS of the surgical tool 234 can also be tracked by the tracking system 222 and processing circuit 260 relative to the haptic object in order to generate controls signals to the robotic arm 232 to confine the surgical tool 234 to a haptic object. In other embodiments, the robotic arm 232 and the surgical tool 234 autonomously make the posterior chamfer cut in coordination with the tracking system 222 as controlled by the processing circuit 260. The surgical tool 234 can thus be used, for example autonomously or by a surgeon as confined to a haptic object, to make the distal cut 502 in femur 206 while the tracking system 222 tracks instantaneous TCP positions in the registered, three-dimensional Euclidean coordinate system of the planned cuts (e.g., as shown in FIGS. 5A-5C).

At step 408, the recorded distal cut plane 700 is determined by the processing circuit 260. The recorded distal cut plane 700 is illustrated in FIG. 7. To determine the recorded distal cut plane 700, the processing system identifies the recorded TCP positions that correspond to the cut made in femur 206 and fits a plane to those points. The TCP positions that correspond to the cut made in femur 206 may be identified as those points that penetrate a virtual bone model of the femur 206 to the greatest extent, that make up a boundary of a 3-D cloud of recorded TCP positions and that corresponds to the planned distal cut 502, and any other point identification approach. A plane may be fit to those positions (i.e., points defined in three-dimensions in the coordinate system of FIGS. 5A-5C) by some suitable plane fitting approach. A statistical approach to fitting a plane to many points (e.g., more than three) may provide an accurate determination of the actual cut made by the surgical tool 234 and characterized as the recorded distal cut plane 700, even where all identified points do not lie in the fit plane. The recorded distal cut plane 700 is thus determined, such that it can be defined in a similar way as the distal cut 502 described with reference to FIG. 5A.

At step 410, the processing system determines the error of the recorded distal cut plane 700 relative to the planned distal cut 502 as in the original surgical plan 600. As shown in FIG. 7A, the recorded distal cut plane 700 deviates from the planned distal cut 502 translationally (i.e., the recorded distal cut plane 700 is 'lower' than the planned distal cut 502 in the cross-sectional view of FIG. 7) and rotationally (i.e., the recorded distal cut plane 700 is not parallel to the planned distal cut 502). While shown as rotational error in the sagittal plane for the sake of visibility in the cross-section of FIG. 7A, the rotational error of the recorded distal cut plane 700 considered at step 410 is a rotation around the y-axis 516 as indicated in FIG. 5A (i.e., a varus/valgus angular error). While the recorded distal cut plane 700 may also have rotational errors about the x-axis 524 and z-axis 520, at step 410 the varus/valgus angular error of the recorded distal cut plane 700 is considered because of the way that a femoral prosthesis interacts with the femur 206 during trialing/implantation. When the prosthesis is placed, the anterior surface 108 and posterior surface 106 substantially restrict anterior-posterior translation in the y-direction, internal/external rotation about the z-axis 516, and flexion/extension rotation about the x-axis 524. The distal surface 102 is left to contribute errors in superior-inferior translation (in the z-direction) and in varus/valgus rotation. Thus, errors in superior-inferior translation and in varus/vulgus rotation are considered at step 410 while other errors are considered in subsequent steps.

To account for these errors, two error terms are calculated in step 410, namely $D_{distal}$ and $A_{y\_distal}$. $D_{distal}$ is calculated as the shortest distance between the centroid of the distal cut 502 and the recorded distal cut plane 700. $D_{distal}$ may also include a directional component (i.e., defined as a vector), or may be measured/defined in a predetermined direction (e.g., along the z-direction, normal to the planned distal cut 502). $A_{y\_distal}$ is calculated as the angle of rotation around the y-axis 516 from the planned distal cut 502 to the recorded distal cut plane 700.

Figure 7B:
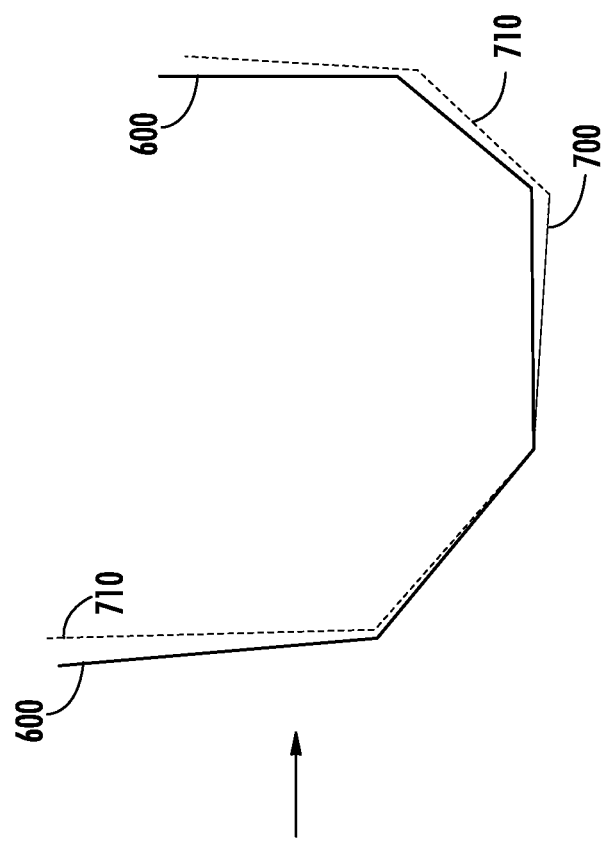
FIGS. 7A-B are cross-sectional views of the planned surgical cuts of FIGS. 5A-6 with a recorded distal cut plane and the planned cuts of a first updated surgical plan as in the process of FIG. 4, according to an exemplary embodiment.
Figure 7A:
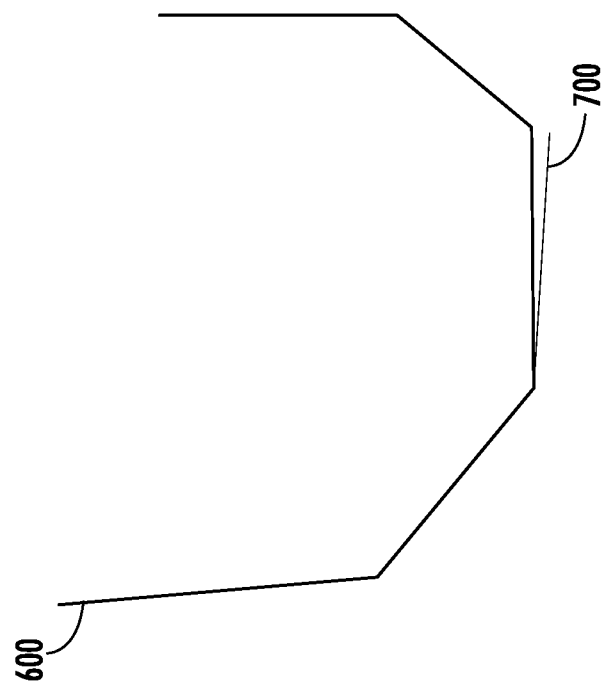

At step 412, the planned posterior chamfer cut 504, posterior cut 506, anterior cut 508, and anterior chamfer cut 510 as in original surgical plan 600 are adjusted based on the calculated error terms to generate first updated surgical plan 710 shown in FIG. 7B. The centroids of the four remaining cuts 504-510 are each translated by $D_{distal}$ along the direction of error (e.g., along the z-direction), and the cuts 504-510 are rotated by $A_{y\_distal}$. This adjustment takes the relative error between the recorded distal cut plane 700 and the remaining cuts 504-510 to zero along the z-direction (superior-inferior translation) and around the y-axis 516 (varus/vulgus rotation), and results in the first updated surgical plan 710 shown in FIG. 7B. In some cases, an error in rotation about the x-axis 724 between the recorded distal cut plane 700 and the remaining cuts 504-510 is still present, and is minimized in subsequent steps.

At step 414, the control object is updated based on the adjusted planned cuts 504-510 of first updated surgical plan 710. For example, in an embodiment where the haptic object includes a planar haptic object for each of the planned cuts 502-510, such that the haptic object is configured to confine the surgical tool 234 substantially to the plane needed to make the corresponding cut, the planar haptic object corresponding to each remaining cut is adjusted to confine the surgical tool 234 substantially to the plane needed to make the adjusted cut in accordance with the first updated surgical plan 710. In some embodiments, to save computational resources, only the control object corresponding to the next planned cut (i.e., according to the sequence of cuts as in process 400) or the next two planned cuts is updated at step 414 (i.e., the posterior chamfer cut and the posterior cut).

At step 416, the surgical system 200 facilitates the posterior chamfer cut according to the first updated surgical plan 710. In some embodiments, the surgical tool 234, confined within a haptic object by robotic arm 232 as controlled by the processing circuit 260 based on tracking information from the tracking system 222, is manipulated by a surgeon to make the posterior chamfer cut 504 as in first updated surgical plan 710. In other embodiments, the robotic arm 232 and the surgical tool 234 autonomously make the posterior chamfer cut in coordination with the tracking system 222 and the processing circuit 260. According to the embodiment of process 400 shown in FIG. 4, the TCP positions need not by tracked in step 416, as the error determination and adjustments steps are not carried out for the posterior chamfer cuts. Skipping these steps (e.g.) for the posterior chamfer cut may save computation resources and avoid delays caused by computation times, without compromising the overall error minimization process. In other embodiments, the TCP tracking, error determination, and plan updating steps (e.g., steps 308-312 of process 300) are carried out for each of the first four of the five femoral cuts or for all planned cuts.

At step 418, the surgical system 200 facilitates the posterior cut while tracking the tool center point (TCP) of the surgical tool 234. Similar to step 406 described above, in step 418 surgical tool 234 can be autonomously controlled or manipulated by a surgeon confined by a haptic object to make the updated posterior cut 506 in femur 206 while the tracking system 222 tracks instantaneous TCP positions in the registered, three-dimensional Euclidean coordinate system of the planned cuts (e.g., as shown in FIGS. 5A-5B).

At step 420, the processing circuit 260 uses the recorded TCP positions to determine a recorded posterior cut plane. The recorded posterior cut plane 800 is illustrated in FIG. 8. As in step 408, and described in more detail in reference thereto, to determine the recorded posterior cut plane 800, the processing system identifies the recorded TCP positions that correspond to the cut made in femur 206 and fits a plane to those points.

At step 422, the processing system determines the error of the recorded posterior cut plane 800 relative to the planned posterior cut 506 as in first updated surgical plan 710. As shown in FIG. 8A, the recorded posterior cut plane 800 deviates from the updated planned posterior cut 506 translationally (i.e., the recorded posterior cut plane 800 is to the right of the updated planned posterior cut 506 in the cross-sectional view of FIG. 8A) and rotationally (i.e., the recorded posterior cut plane 800 is not parallel to the planned posterior cut 506). The rotational deviation of the recorded posterior cut plane 800 has two components: a rotation around the z-axis 520 (internal/external angular error) as illustrated in FIG. 5B and a rotation around the x-axis 524 (flexion/extension angular error) as illustrated in FIG. 5C. Three error components are therefore determined for the recorded posterior cut plane 800, namely $D_{posterior}$, $A_{x\_posterior}$, and $A_{z\_posterior}$. $D_{posterior}$ is calculated as the shortest distance from the centroid of the planned posterior cut 506 to the recorded posterior cut plane 800. $A_{x\_posterior}$ is calculated as the angle of rotation around the x-axis 524 from the planned posterior cut 506 to the recorded posterior cut plane 800. $A_{z\_posterior}$ is calculated as the angle of rotation around the z-axis 520 from the planned posterior cut 506 to the recorded posterior cut plane 800.

At step 424, the processing circuit 260 adjusts the first updated surgical plan 710 (i.e., for the anterior cut and the anterior chamfer cuts) based on the calculated error components of the recorded posterior cut plane 800 to get second updated surgical plan 810 shown in FIG. 8B. Modifications based on $D_{posterior}$, $A_{x\_posterior}$, and $A_{z\_posterior}$ are weighted based on a weighted parameter w, to result in a reduction in of cutting error in the posterior cut of (w*100)%. The parameter w may be determined from experimental results or some other approach to determining an optimal value of w. For example, w may be a number between zero and 1. To get from the first updated surgical plan 710 to the second updated surgical plan 810, the location of the remaining cuts (i.e., anterior cut 508 and anterior chamfer cut 510) are translated by $w*D_{posterior}$, and the planned cuts 508-510 are rotated around the x-axis by $w*A_{x\_posterior}$ and around the z-axis by $W*A_{z\_posterior}$ (in the directions of error minimization, i.e., the same directions that posterior cut 506 would have to be translated/rotated to align with recorded posterior cut plane 800).

At step 426, the control object is updated to correspond to the second updated surgical plan 810. As for step 414, in an embodiment where the control object is a haptic object that includes a planar haptic object for each of the planned cuts 502-510, such that the haptic object is configured to confine the surgical tool 234 substantially to the plane needed to make the corresponding cut, the planar haptic object corresponding to each remaining cut is adjusted to confine the surgical tool 234 substantially to the plane needed to make the adjusted cut in accordance with the second updated surgical plan 810. In some embodiments, each remaining cut (i.e., the anterior and anterior chamfer cuts) may have a corresponding planar control object that is adjusted by $w*D_{posterior}$, $w*A_{x\_posterior}$, and $w*A_{z\_posterior}$.

At step 428, the surgical system 200 facilitates the anterior cut while tracking TCP positions. Similar to steps 406 and 418 described above, in step 428 surgical tool 234 can be autonomously controlled or manipulated by a surgeon confined by a haptic object to substantially follow the second updated surgical plan 810 to make the updated planned anterior cut 508 in femur 206 while the tracking system 222 tracks instantaneous TCP positions in the registered, three-dimensional Euclidean coordinate system of the planned cuts (e.g., as shown in FIGS. 5A-5B).

At step 430, the processing system determines the recorded anterior cut plane 900. The recorded anterior cut plane 900 is illustrated in FIG. 9A. As in step 408, and described in more detail in reference thereto, to determine the recorded anterior cut plane 900, the processing system identifies the recorded TCP positions that correspond to the cut made in femur 206 and fits a plane to those points.

At step 432, the processing circuit 260 determines the error of the recorded anterior cut plane 900 relative to the updated planned anterior cut 508 of second updated surgical plan 810. As shown in FIG. 9A, the recorded anterior cut plane 900 deviates from the updated planned anterior cut 508 translationally (i.e., the recorded anterior cut plane 900 is to the left of the updated planned anterior cut 508 in the cross-sectional view of FIG. 9) and rotationally (i.e., the recorded anterior cut plane 900 is not parallel to the planned anterior cut 508). The rotational deviation of the recorded anterior cut plane 900 has two components: a rotation around the z-axis 520 (internal/external angular error) as illustrated in FIG. 5B and a rotation around the x-axis 524 (flexion/extension angular error) as illustrated in FIG. 5C. Three error components are therefore determined for the recorded anterior cut plane 900, namely $D_{anterior}$, $A_{x\_anterior}$, and $A_{z\_anterior}$. $D_{anterior}$ is calculated as the shortest distance from the centroid of the planned anterior cut 508 to the recorded anterior cut plane 900. $A_{x\_anterior}$ is calculated as the angle of rotation around the x-axis 524 from the updated planned anterior cut 508 to the recorded anterior cut plane 900. $A_{z\_anterior}$ is calculated as the angle of rotation around the z-axis 520 from the updated planned anterior cut 508 to the recorded anterior cut plane 900.

At step 434, the processing circuit 260 adjusts the surgical plan for the anterior chamfer cut 510 based on the calculated error components of the recorded anterior cut plane 900 to get third updated surgical plan 910 shown in FIG. 9B. To obtain third updated surgical plan 910, the updated planned anterior chamfer cut 510 of second updated surgical plan 810 is translated by $(1-w)*D_{anterior}$, rotated around the x-axis by $(1-w)*A_{x\_anterior}$ and rotated around the z-axis by $(1-w)*A_{z\_anterior}$ (in the directions of error minimization, i.e., the same directions that planned anterior cut 510 as in second updated surgical plan 810 would have to be translated/rotated to align with recorded anterior cut plane 900). An updated plan for the anterior chamfer cut 510 is thereby obtained.

At step 436, the processing circuit 260 updates the control object based on the third updated surgical plan 910. For example, in some embodiments, a planar haptic object corresponding to the anterior chamfer cut 510 is adjusted by $(1-w)*D_{anterior}$, $(1-w)*A_{x\_anterior}$, and $(1-w)*A_{z\_anterior}$. The processing circuit 260 thereby generates a control object suitable for facilitating the anterior chamfer cut 510 according to third updated surgical plan 910.

Figure 10:
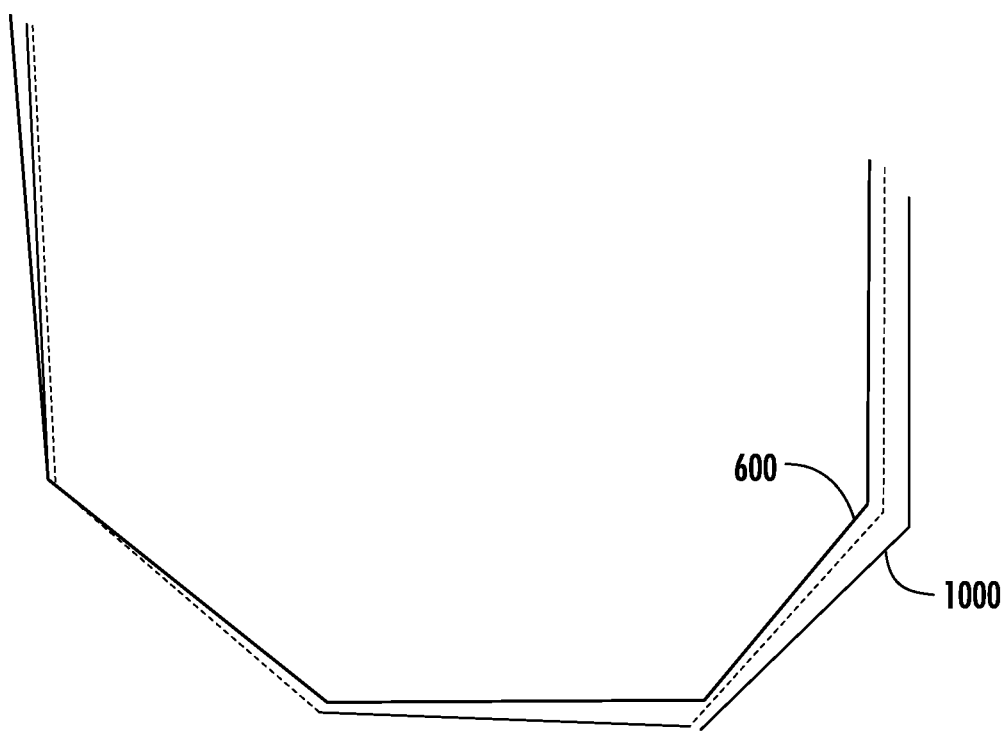
FIG. 10 is a cross-sectional view of the planned surgical cuts of FIGS. 5A-6 with a visualization of the final completed cuts, according to an exemplary embodiment.

At step 438, the surgical system 200 facilitates the anterior chamfer cut to carry out third updated surgical plan 910. Similar to step 416 described above, in step 428 surgical tool 234 can be autonomously controlled or manipulated by a surgeon confined by a haptic object to make the anterior chamfer cut 510 in femur 206. In some embodiments, the TCP positions of the surgical tool 234 are tracked while the anterior chamfer cut is made for the sake of overall error assessment and/or other medical purposes. FIG. 10 shows the final completed cuts 1000 relative to the original surgical plan 600. As shown, the relative error between the cuts has been lessened by the intraoperative assessment and plan updates, for example by shifting the anterior cut towards the posterior cut and rotating it to better preserve the originally-planned overall shape of the cuts. In this way, intraoperative updates to the plan and adjustments as described herein can contribute to the overall success of the arthroplasty procedure.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A method, comprising:
    collecting a cloud of points reached by a cutting tool during completion of the first stage of modifying a bone with the cutting tool;
    fitting a surface to a side of the cloud of points such that the surface corresponds to an actual cut of the bone completed during the first stage of the bone with the cutting tool;
    generating a planned cut to be completed during a second stage of modifying the bone with the cutting tool based on a location or rotation of the surface, the planned cut offset from the surface; and
    assisting, by a robot controlled using the planned cut, the cutting tool in executing the second stage of modifying the bone with the cutting tool.

2. The method of claim 1, wherein assisting, by the robot, the cutting tool comprises providing, by the robot, force feedback that constrains the cutting tool to the planned cut to assist the cutting tool in executing the second stage.

3. The method of claim 1, wherein generating the planned cut for the second stage based on the location or rotation of the surface comprises comparing the location or rotation of the surface to a planned location or planned rotation for a first cut of the first stage.

4. The method of claim 1, wherein generating the planned cut for the second stage comprises adjusting the planned cut for the second stage based on an error between the location or rotation of the surface and a planned location or planned rotation for a first cut of the first stage of the procedure.

5. The method of claim 1, wherein collecting the cloud of points comprises tracking, by a tracking system, the cutting tool while the cutting tool is used to execute the first stage of modifying the bone with the cutting tool.

6. The method of claim 1, wherein fitting the surface to the side of the cloud of points comprises identifying a subset of the points which correspond to deepest movement of the cutting tool into the bone and fitting a plane to the subset of the points.

7. The method of claim 1, wherein the generating the planned cut based on the location or rotation of the surface comprises achieving a target relationship between the actual cut and the planned cut.

8. The method of claim 7, wherein the procedure comprises preparing the bone, via at least the first stage and the second stage, to mate with a joint replacement implant, and wherein the target relationship between the actual cut and the planned cut is based on a geometry of the joint replacement implant.

9. One or more non-transitory computer-readable media storing instructions that, when executed by one or more processors, cause the one or more processors to perform operations comprising:
    fitting a surface to a side of a cloud of points reached by a cutting tool during completion of a first stage of modifying a bone with the cutting tool such that the surface corresponds to a bone surface created by the first stage of modifying the bone;
    generating a plan for a second stage of modifying the bone with the cutting tool based on an assessment of the surface such that the plan for the second stage is based on a result of the first stage of modifying the bone with the cutting tool as represented by the surface; and
    controlling a robot using the plan, wherein the cutting tool interfaces with the robot such that the robot assists the cutting tool in executing the second stage of modifying the bone based on the plan.

10. The one or more non-transitory computer-readable media of claim 9, wherein the operations comprise performing the assessment of the surface by comparing the surface to a planned first cut associated with the first stage of modifying the bone with the cutting tool.

11. The one or more non-transitory computer-readable media of claim 10, wherein generating the plan for the second stage comprises adjusting a planned second cut based on a deviation of the surface from the planned first cut.

12. The one or more non-transitory computer-readable media of claim 9, wherein using the plan to assist the cutting tool in executing the second stage of modifying the bone comprises controlling a robotic device in accordance with the plan.

13. The one or more non-transitory computer-readable media of claim 9, wherein modifying the bone comprises preparing the bone to mate with a joint replacement implant, and wherein generating a plan for a second stage of modifying the bone with the cutting tool based on an assessment of the surface is further based on a geometric relationship between a first portion of the joint replacement implant to be mated with a first portion of the bone prepared in the first stage and a second portion of the joint replacement implant to be mated with a second portion of the bone to be prepared in the second stage.

14. A surgical system, comprising:
a robotic arm;
a cutting tool configured to interface with the robotic arm; and
circuitry programmed to:
collect a cloud of points reached by the cutting tool during a first stage of modifying a bone with the cutting tool;
fit a surface to a side of the cloud of points such that the surface corresponds to a bone surface created by the first stage of modifying the bone;
generate a plan for a second stage of modifying the bone with the cutting tool based on a location or rotation of the surface; and
control the robotic arm using the plan to assist the cutting tool in executing the second stage of modifying the bone.

15. The surgical system of claim 14, wherein the circuitry is programmed to generate the plan for the second stage based on the location or rotation of the surface by comparing the location or rotation of the surface to a planned location or planned rotation for a first cut of the first stage of modifying the bone.

16. The surgical system of claim 14, wherein modifying the bone with the cutting tool prepares the bone to receive an implant.

17. The surgical system of claim 14, wherein the surface corresponds to an actual first cut made during the first stage, wherein the plan for the second stage comprises a planned second cut to be made during the second stage, and wherein the circuitry is programmed to generate the plan further based on a target relationship between the actual first cut and the planned second cut.

18. The surgical system of claim 14, wherein the circuitry is further programmed to obtain the cloud of points based on measured joint angles of the robotic arm.

* * * * *